United States Patent [19]
Van Antwerp

[11] Patent Number: 5,538,511
[45] Date of Patent: Jul. 23, 1996

[54] INDWELLING CATHETER WITH STABLE ENZYME COATING

[75] Inventor: William P. Van Antwerp, Westchester, Calif.

[73] Assignee: Minimed Inc., Sylmar, Calif.

[21] Appl. No.: 428,944

[22] Filed: Apr. 25, 1995

Related U.S. Application Data

[63] Continuation of Ser. No. 221,934, Apr. 1, 1994.
[51] Int. Cl.⁶ .............................. A61M 5/32; A61F 2/00
[52] U.S. Cl. ............................ 604/265; 424/423
[58] Field of Search ...................... 604/265, 264, 604/266, 892.1; 424/422–426, 448

[56] References Cited

U.S. PATENT DOCUMENTS

| | | |
|---|---|---|
| 4,879,135 | 11/1989 | Greco et al. . |
| 5,001,062 | 3/1991 | Larsson et al. . |
| 5,019,393 | 5/1991 | Ito et al. ................................. 424/423 |
| 5,061,237 | 10/1991 | Gessler et al. . |
| 5,244,799 | 9/1993 | Anderson . |
| 5,298,255 | 3/1994 | Sawamoto et al. . |

FOREIGN PATENT DOCUMENTS

0366564A3  of 0000  European Pat. Off. .

Primary Examiner—John D. Yasko
Assistant Examiner—Adam J. Cermak
Attorney, Agent, or Firm—Kelly Bauersfeld & Lowry

[57] ABSTRACT

An improved indwelling catheter adapted for long-term usage includes a stable enzyme coating to prevent occlusion of the catheter lumen. The enzyme coating includes a fibrinolytic and/or lipolytic enzyme incorporated in a catheter coating to resist or control proteolytic degradation, thereby maintaining the enzyme in an active state for dissolving clots and occlusions within the catheter lumen over an extended period of time.

7 Claims, 3 Drawing Sheets

INDWELLING CATHETER WITH STABLE ENZYME COATING

This is a continuation of application Ser. No. 08/221,934, filed Apr. 1, 1994.

BACKGROUND OF THE INVENTION

This invention relates generally to improvements in catheters for use in delivering medical fluids to a patient. More particularly, this invention relates to an improved catheter and related methods of manufacture, wherein the improved catheter has a stabilized enzyme coating for long-term interaction with body fluids to prevent and/or dissolve clots and occlusions within the catheter lumen.

Catheters are well-known in the medical arts for use in delivering medical fluids to or drawing body fluids from a patient. In one typical form, the catheter comprises an elongated tubular element adapted for transcutaneous placement, normally with the assistance of a withdrawable stylet needle. The catheter defines a narrow lumen or passage permitting transcutaneous fluid transfer to or from the patient. In another typical application, the catheter is implanted into the patient in association with an implantable infusion pump or similar instrument for programmed delivery of a selected medication such as insulin over an extended period of time. One such implantable infusion pump including an implantable catheter is shown, by way of example, in U.S. Pat. Nos. 4,373,527 and 4,573,994. In either case, the catheter is commonly constructed from a biocompatible polymer material, such as a medical grade silicone rubber.

In many patient treatment applications, it is necessary or desirable for the catheter to remain in place for an extended period of time which may range from several days to several years. Such long-term indwelling catheters are routinely used, for example, for monitoring patient blood components, dialysis and hemodialysis, parenteral feeding, delivery of certain medications, etc. However, the catheter lumen is susceptible to occlusion which occurs as a result of complex interactions involving the catheter material, and the simultaneous presence of infusion and body fluids. In some forms, catheter occlusions appear to consist primarily of fibrin-based clots, whereas in other forms the occlusions include lipid-based substances. When an occlusion occurs, the catheter must be replaced or the lumen otherwise cleared before infusion of the medical fluids can be resumed. Occlusion removal in an implanted catheter can be difficult, and removal is not a desirable alternative.

In the past, several methods have been proposed in an effort to prevent catheter occlusions or otherwise to clear the catheter lumen after a blockage has occurred. More specifically, heparin is well-known for its anticoagulant characteristics, and is frequently used to prevent clot formation within the catheter lumen. In one approach, the catheter lumen is simply dipped in a heparin solution before patient placement, with the dip coating being generally effective to prevent localized clotting over a relatively short period of time until the heparin is degraded upon contact with body fluids. In an alternative approach, the catheter is periodically flushed with a heparin solution in a manner leaving a quantity of residual heparin within the catheter lumen to resist clot formation when the catheter is not in use. Unfortunately, heparin is ineffective to dissolve clots and/or other occlusions after formation thereof, whereby heparin usage has not provided satisfactory catheter occlusion control. Moreover, heparin has not been approved for use with some medications, such as insulin.

Alternative occlusion control methods have utilized a fibrinolytic enzyme such as a kinase enzyme known to be effective in dissolving fibrin-based clots. In this regard, dip coating of the catheter in a solution containing a fibrinolytic enzyme has been shown to be effective in preventing and/or dissolving clots along the narrow catheter lumen. However, in the presence of body fluids, the fibrinolytic enzyme degrades rapidly and is thus ineffective for long-term occlusion control. Any clots formed subsequent to enzyme degradation are extremely difficult to dissolve, since it is difficult to deliver additional enzyme solution to the blockage site along the catheter lumen.

In addition, it is believed that occlusions forming along the catheter lumen are frequently attributable at least in part and perhaps primarily to accumulation of lipid-based substances, with fibrin-based clotting having a lesser role in formation of the blockage. Previous occlusion control methods involving the use of heparin or fibrinolytic enzymes are ineffective to break down and dissolve a lipid-based occlusion.

There exists, therefore, a significant need for further improvements in indwelling catheters and related methods for preventing and/or dissolving catheter occlusions, particularly for use in providing occlusion control over an extended period of time. The present invention fulfills these needs and provides further related advantages.

SUMMARY OF THE INVENTION

In accordance with the invention, an improved indwelling catheter and related production method are provided, wherein the catheter includes a stable and substantially immobilized enzyme coating to prevent formation of and/or to dissolve occlusions along the catheter lumen. The enzyme coating comprises a selected fibrinolytic and/or lipolytic enzyme applied to the catheter, in combination with means for preventing or otherwise regulating proteolytic degradation in response to enzyme interaction with body fluids. The thus-protected enzyme exhibits relatively stable characteristics, with long-term effectiveness in the prevention and/or dissolution of catheter occlusions.

In one form, the selected enzyme is applied to indwelling surfaces of the catheter as a thin micellar coating. A porous encapsulant such as a porous silicone rubber film is then applied to the catheter to cover and encapsulate the micellar enzyme. The porosity of the encapsulant film is controlled to isolate the enzyme from significant interaction with proteolytic body fluids, while permitting diffusion of other body fluid constituents to activate the enzyme for purposes of preventing or dissolving an occlusion. For example, by controlling the porosity of the encapsulant film, a fibrinolytic enzyme can be protected against proteolytic degradation yet interact with plasminogen to produce plasmin which is effective in dissolving fibrin-based clots.

In an alternative form, the selected enzyme in particulate form is coated with an encapsulant shell of starch-based material or the like, and variable coating thickness. The resultant capsules are bonded to the polymeric surface of the catheter by silicone chemistry, such as coating the capsules and catheter with different silanes adapted for stable bonding upon contact therebetween. When the catheter is used, the encapsulant shells dissolve slowly to expose the enzyme in a gradual manner over an extended period of time.

In a still further preferred embodiment of the invention, the selected enzyme is mixed with albumin to form a slurry. The albumin is then cross-linked with the enzyme at the surface of the catheter, resulting in a cross-link chemical bond, by applying the slurry to a gel of silane and a selected aldehyde on the catheter surface. The cross-linked enzyme is thus integrated into a membrane-like matrix on the surface of the catheter where it is available for occlusion control but otherwise shielded from proteolytic degradation.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 7a is an enlarged fragmented sectional view corresponding with the coated particle identified in FIG. 7 by the encircled region 7a;

DETAILED DESCRIPTION OF THE PREFERRED EMBODIMENTS

Figure 6:
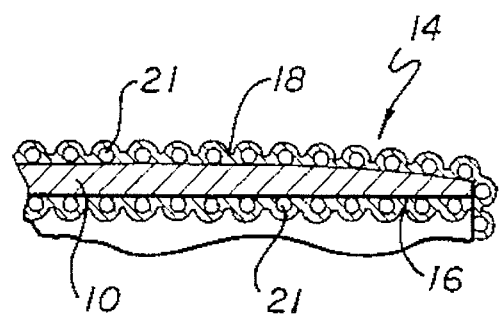

As shown in the exemplary drawings, an improved indwelling catheter referred to generally by the reference numeral 10 is provided for long-term infusion of medical fluids to a patient 12. The catheter 10 includes a stable, substantially immobilized enzyme-containing coating 14 as depicted, for example, in FIG. 6, for preventing and/or dissolving occlusions. Proteolytic and/or chemical hydrolysis between the enzyme coating and patient body fluids, which would otherwise result in rapid enzyme degradation and deactivation, is substantially prevented or otherwise controlled in a manner rendering the enzyme available for effective long-term occlusion control.

Figure 1:
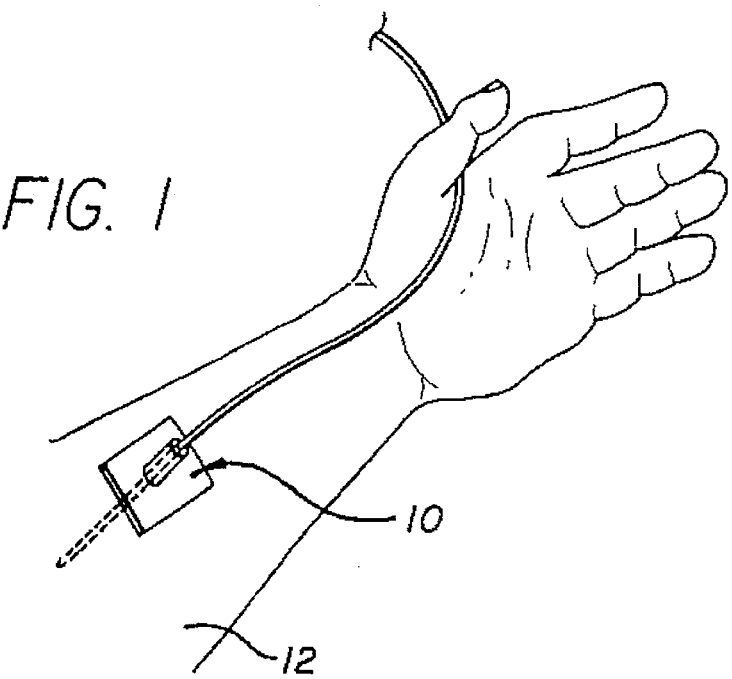
FIG. 1 is a perspective view illustrating a typical catheter installed transcutaneously for infusing medication to a patient.
Figure 2:
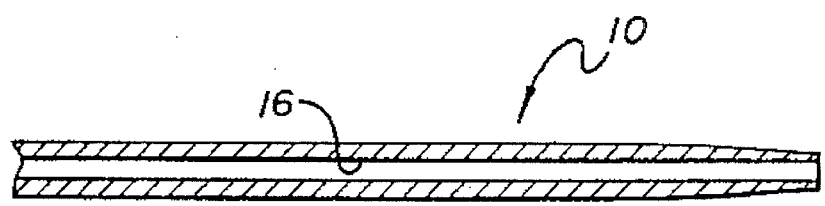
FIG. 2 is a enlarged fragmented sectional view illustrating the cross sectional geometry of an indwelling portion of the catheter shown in FIG. 1.

The catheter 10 shown in FIGS. 1 and 2 has a generally conventional construction to include an elongated tubular member adapted for transcutaneous placement on the patient 12, for use in infusing medical fluids to or drawing body fluids from the patient. The catheter 10 is typically installed with the assistance of an elongated stylet needle (not shown) or the like which can be withdrawn from the catheter lumen 16 subsequent to catheter placement. It will be understood, however, that the invention contemplates other types of catheters, particularly such as an implantable device adapted for use in combination with an implantable medication infusion pump or the like to deliver medication to a patient over an extended period of time. In either form, the catheter 10 is commonly constructed from a polymeric material, such as medical grade silicone rubber, polyethylene, or the like.

In the course of normal catheter usage, occlusions can form along the catheter lumen 16, particularly near the tip end thereof, as a result of complex interactions involving infusion fluids, body fluids, and the polymeric catheter material. Such occlusions are commonly associated with fibrin-based clots, although it is believed that lipid-based substances can also play a major and even dominant role in blockage formation. The present invention relates to apparatus and method for preventing and/or dissolving such occlusions over an extended period of catheter usage.

In general terms, and in accordance with the present invention, a selected enzyme effective to prevent or dissolve a catheter occlusion is applied as an integral part of the coating 14 on the catheter 10. A fibrinolytic enzyme such as a kinase enzyme may be used for dissolving fibrin-based clots. Examples of kinase enzymes suitable for this purpose include urokinase, streptokinase, and tissue plasminogen activator (TPA). Alternatively, a lipolytic enzyme such as phospholipase may be used for dissolving a lipid-based occlusion. A combination of such fibrinolytic and lipolytic enzymes may also be used. In each case, in the preferred form, the selected enzyme or combination of enzymes is isolated or otherwise protected against rapid proteolytic or chemical hydrolysis breakdown in the presence of body fluid, thereby sustaining enzyme activity for long-term effectiveness in preventing catheter occlusions.

FIGS. 3–6 illustrate one preferred form of the invention, wherein the selected enzyme is mechanically trapped or retained against the surface of the catheter 10 by an encapsulating film 18 selected for secure film adhesion to the polymeric catheter material. The encapsulating film 18 is produced with a controlled porosity to protect and isolate the enzyme from proteolytic components in body fluid, while permitting enzyme activity to reduce or eliminate catheter blockages.

Figure 3:
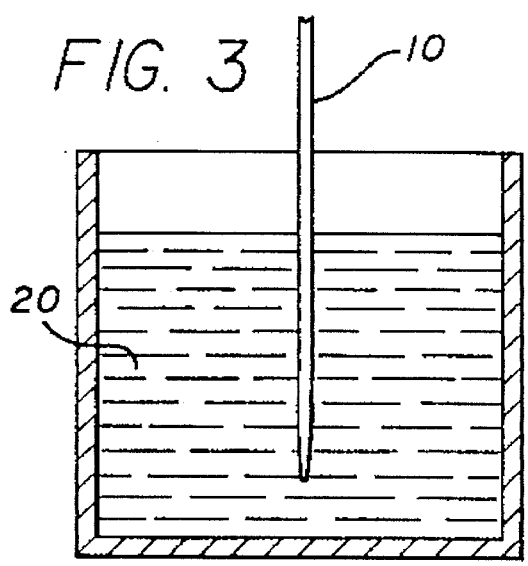
FIGS. 3–6 illustrate a sequence of process steps for applying a stable enzyme coating onto the surface of a catheter, in accordance with one preferred form of the invention.

More specifically, FIG. 3 illustrates immersion of catheter 10 into a prepared enzyme slurry or emulsion 20. In this regard, the enzyme is commonly available in particulate form, having a particle size ranging on the order of one to fifteen microns. The enzyme particles are mixed in a liquid carrier such as water to produce the emulsion 20 shown in FIG. 3. Upon withdrawal of the catheter 10 from the enzyme emulsion 20, the catheter surface is allowed to dry resulting in adherence of the enzyme to the catheter in a micellar array of microsphere particles 21, as shown in exaggerated form in FIG. 4.

Figure 5:
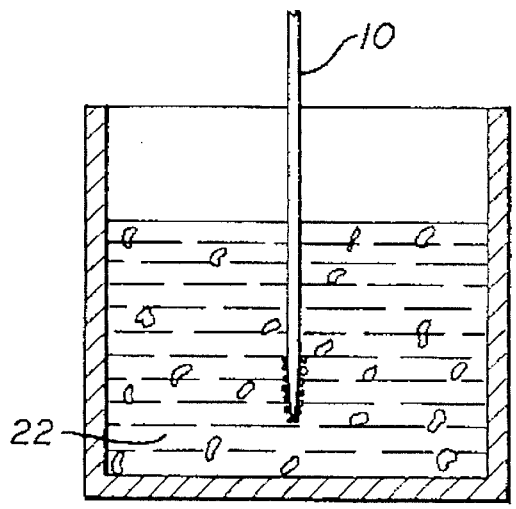

The encapsulating film 18 is prepared as shown in FIG. 5, in the form of dilute silicone rubber. In particular, in accordance with one preferred form of the invention, a silicone rubber elastomer and curing agent such as those marketed by Dow Corning Corporation of Midland, Mich., under the designation Silastic MDX4-4210, is mixed in a ratio of about 35 to 1 by volume, and then diluted by addition of water. The resultant solution 22, when applied to the catheter and cured in film form, adheres securely to the polymeric catheter material while providing a controlled porosity in accordance with the proportion of water addition. A preferred water proportion is on the order of 30 to 35 percent, to provide a resultant film pore size of about 1,000 Å.

Figure 4:
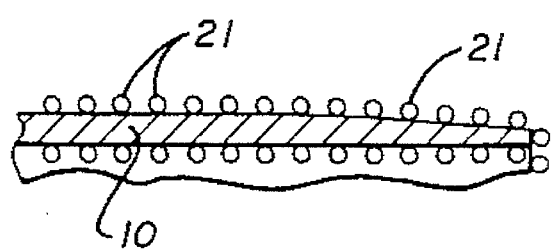

The catheter 10 prepared in accordance with FIGS. 3 and 4, is dipped into the uncured film solution 22 of FIG. 5, and then withdrawn to permit curing of the encapsulant film 18 thereon. As shown in exaggerated form in FIG. 6, the silastic-based film adheres to the catheter in the spaces between the enzyme micells 21, while providing the protective film 18 which encapsulates and isolates the enzyme particles from adjacent body fluids. The controlled porosity of the film 18 permits diffusion passage of body fluid constituents to activate the enzyme, such as plasminogen which results in production of plasmin for solubilizing fibrin-based clots. Larger and more complex molecules such as proteolytic-based substances within the body fluid are isolated by the film 18 from the enzyme, thereby shielding the enzyme from significant proteolytic body fluid breakdown.

FIGS. 7–10 illustrate an alternative preferred form of the invention, wherein the enzyme particles 24 are integrated into time release capsules 26 which are mounted in turn by chemical bonding onto the catheter surface. The capsules 26 include variable coating thicknesses for dissolution at different times in the presence of body fluids, thereby exposing the encapsulated enzyme particles 24 over an extended time period for occlusion control.

Figure 7:
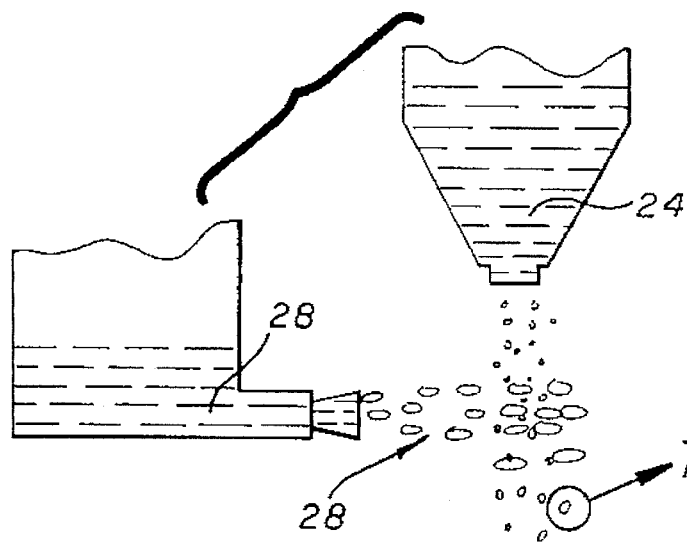
FIG. 7 illustrates an alternative preferred form of the invention, wherein a coating solution is sprayed onto falling enzyme particles.
Figure 7A:
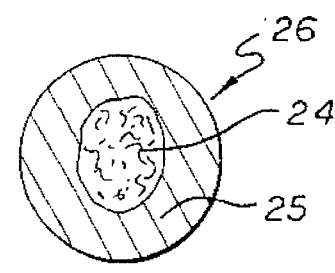
Figure 8:
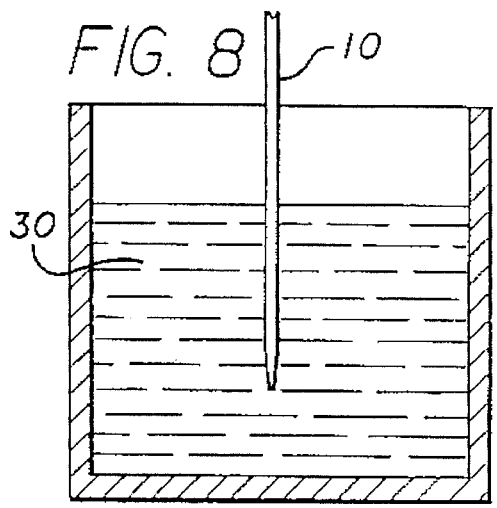
FIGS. 8–10 illustrate a sequence of further process steps, for applying the coated enzyme particles of FIGS. 7 and 7a to the catheter.

FIG. 7 illustrates capsule formation by spraying a stream 28 of a coating solution through an intersecting stream of falling enzyme particles 24. A preferred encapsulant coating solution comprises a starch-based substance such as a selected polysaccharide mixed within a non-protein or aprotic solvent such as acetonytrile. Alternatively, enzyme particles 24 may be blown through an encapsulant bath. In either case, the resultant enzyme-containing capsules 26 are produced with a shell 25 having a variable thickness ranging on the order of about 0.02 to 7 microns.

Figure 9:
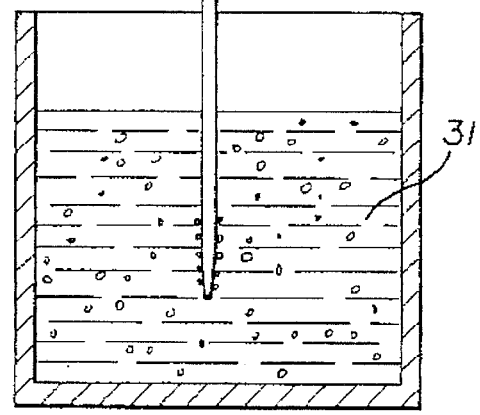

The capsules 26 are then bonded to the polymeric catheter material by silicone chemistry. More specifically, the catheter 10 and the capsules 26 are surface-coated with silane compounds adapted for secure bonding first to the polymeric catheter material and then in turn to the capsules 26. As an example, the catheter 10 is dip coated (FIG. 8) with a first silane compound 30 such as mercaptosilane having a second functional group for covalent bonding with the catheter material. The capsules 26 are coated as by spraying with a second and different silane compound (not shown), such as a long alkylamino silane. The thus-coated capsules are then chemically bonded to the silane-coated catheter by immersing the catheter in a dilute hydrochloric acid solution 31 and with the capsules 26 added thereto (FIG. 9).

Figure 10:
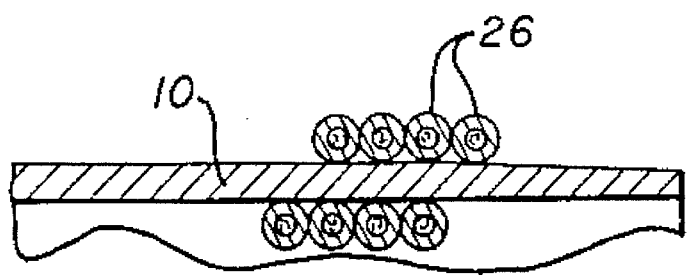

FIG. 10 illustrates in enlarged and exaggerated form, an array of the time release capsules 26 securely bonded to the exterior of the catheter 10. In use, the encapsulant material on the capsules 26 is of varying thickness and dissolves in the presence of body fluid, resulting in time-release exposure of the enzyme particles 24 over an extended time period, for corresponding occlusion control over an extended time period.

Figure 11:
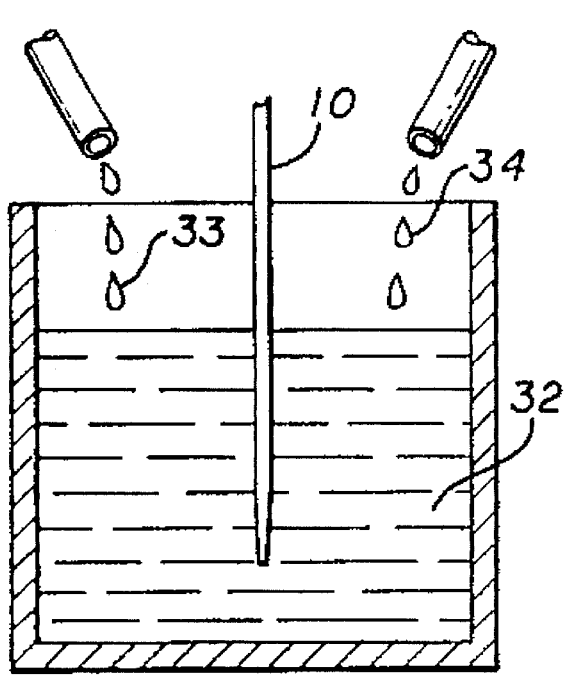
FIGS. 11–13 illustrate a sequence of process steps for applying the stable enzyme coating to the surface of a catheter, in accordance with a still further alternative preferred form of the invention.
Figure 12:
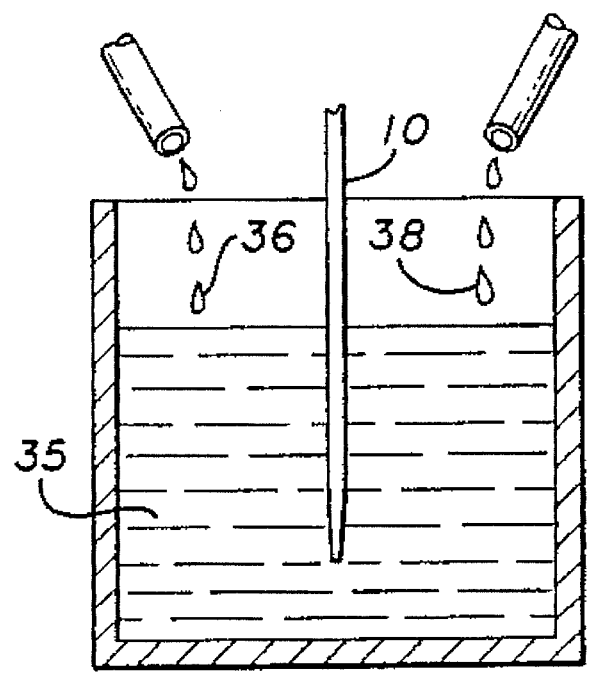
Figure 13:
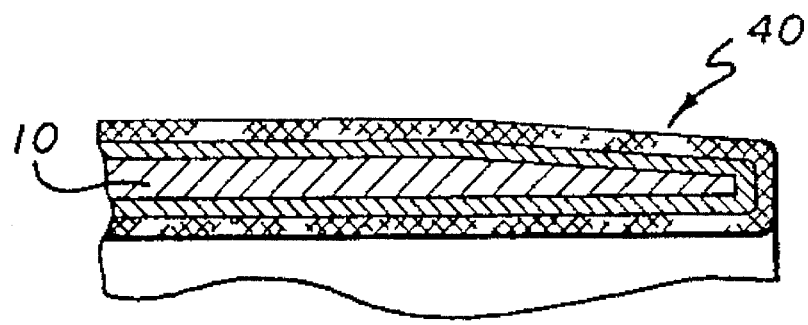

FIGS. 11–13 depict a further alternative preferred form of the invention, wherein the enzyme is securely attached by cross-link bonding to the polymeric catheter material. The cross-link bond is in a matrix with a serum protein such as albumin, which has been found to shield or isolate the enzyme from proteolytic breakdown in the presence of body fluids.

FIG. 11 illustrates dip immersion of the catheter 10 into a solution 32 prepared from a selected silane 33 and a selected aldehyde 34 such as glutaraldehyde or formaldehyde. This initial surface coating on the catheter is securely and covalently bonded to the polymeric catheter material by means of the silane group in the same manner as previously described with respect to FIG. 8. However, in this embodiment, the silane also bonds chemically with the aldehyde. The thus-coated catheter is then dip immersed into a gel solution 35 formed from the selected enzyme 36 and a serum protein such as albumin 38, in a saline solution (FIG. 12) at a concentration of about five percent albumin. A cross-linked membrane 40 (FIG. 13) is thus produced on the surface of the catheter 10, wherein the membrane cross-links the enzyme with the albumin, by means of the aidehyde, to provide a proteolytic resistant structure. However, the enzyme is available for solubilizing catheter occlusions.

With a fibrinolytic enzyme, the enzyme combines with plasminogen available in patient body fluid to produce plasmin. The plasmin cooperates in turn with fibrin present in a fibrin-based clot to produce soluble fibrinogen and other constituents. In effect, the enzyme thus combines with available plasminogen to dissolve a fibrin-based clot. By contrast, with a lipolytic enzyme, the enzyme combines with grease or soap-like phospholipids produced in the presence of body fluids and certain medications, to produce soluble lipase compounds. For example, zinc compounds are commonly used to stabilize certain medications such as insulin, wherein such zinc compounds are believed to combine with phospholipids in body fluid to generate a soap-like lipid-based substance which can accumulate within and occlude the catheter lumen. In the presence of the lipolytic enzyme, the occlusion is dissolved. In the present invention, the selected enzyme applied to the catheter may comprise a fibronolytic or lipolytic enzyme, or a combination thereof.

A variety of further modifications and improvements to the present invention will be apparent to those skilled in the art. AccordinglY, no limitation on the invention is intended by way of the foregoing description and accompanying drawings, except as set forth in the appended claims.

What is claimed is:

1. A catheter, comprising:

an elongated tubular element formed from a polymeric material and adapted for patient placement, said tubular element defining a catheter lumen; and a surface coating applied to said tubular element on at least a portion of the surface thereof, said surface coating including at least one enzyme effective to dissolve occlusions along said catheter lumen, and means for protecting said enzyme against short-term degradation upon contact with patient body fluids;

said at least one enzyme comprising a substantially micellar array of enzyme particles on said tubular element, and further wherein said enzyme protecting means comprises a porous encapsulant film covering said enzyme particles and adhering securely to said tubular element, said encapsulant film having a controlled porosity to permit diffusion passage of body fluid constituents effective to activate the enzyme for occlusion control while substantially shielding the enzyme against degradation;

said at least one enzyme being selected from the group consisting of urokinase, streptokinase, tissue plasminogen activator (TPA) and phospholipase, and mixtures thereof.

2. The catheter of claim 1 wherein said encapsulant film comprises dilute silicone rubber.

3. A method of applying an enzyme coating to a polymeric catheter, said method comprising the steps of:

applying a selected enzyme to at least a portion of the surface of the catheter in a substantially micellar array, said at least one enzyme being selected from the group consisting of urokinase, streptokinase, tissue plasminogen activator (TPA) and phospholipase, and mixtures thereof; and encapsulating the micellar array of enzyme with a porous encapsulant film covering the enzyme and adhering to the catheter to retain the enzyme against the catheter surface, for activation upon diffusion passage of patient body fluid constituents to dissolve catheter occlusions.

4. The method of claim 3 wherein said step of applying the enzyme in micellar array to the catheter comprises mixing enzyme particles with water to form an enzyme slurry, dipping the catheter into the enzyme slurry to coat a portion of the catheter surface with the enzyme slurry, and allowing the enzyme slurry to dry on the catheter.

5. The method of claim 3 wherein said step of encapsulating the micellar array of enzyme comprises preparing a film solution containing silicone rubber elastomer and curing agent, dipping the catheter with micellar enzyme array thereon into the film solution to form the encapsulant film, and allowing the encapsulant film to cure in place on the catheter.

6. The method of claim 5 wherein said film solution preparing step comprises mixing the film solution with substantial excess elastomer.

7. The method of claim 6 wherein said film solution preparing step further includes diluting the film solution with water.

* * * * *